United States Patent [19]

Kuze et al.

[11] Patent Number: 4,676,897
[45] Date of Patent: Jun. 30, 1987

[54] SOLUBILIZATION CHROMATOGRAPHY

[75] Inventors: Shuichi Kuze; Tamotsu Inomata; Setsuo Muramoto; Hisayuki Ikeda, all of Tokyo, Japan

[73] Assignee: Yokogawa Hokushin Electric Corporation, Tokyo, Japan

[21] Appl. No.: 906,146

[22] Filed: Sep. 11, 1986

[30] Foreign Application Priority Data

Sep. 26, 1985 [JP] Japan .................................. 60-213337
Oct. 9, 1985 [JP] Japan .................................. 60-225850
Oct. 9, 1985 [JP] Japan .................................. 60-225852

[51] Int. Cl.$^4$ .............................................. B01D 15/08
[52] U.S. Cl. .................................. 210/198.2; 210/659;
204/180.1; 204/183.3; 204/299 R; 422/70
[58] Field of Search ............. 204/180.1, 183.3, 299 R;
210/198.2, 656, 659; 422/70

[56] References Cited

U.S. PATENT DOCUMENTS

| | | | |
|---|---|---|---|
| 3,140,714 | 7/1964 | Murphy | 204/183.3 |
| 3,782,078 | 1/1974 | Jerpe | 210/198.2 |
| 4,028,056 | 7/1977 | Snyder | 210/198.2 |
| 4,107,041 | 8/1978 | Karlson | 210/198.2 |
| 4,315,812 | 2/1982 | Karlson | 204/299 R |
| 4,323,439 | 4/1982 | O'Farrell | 204/183.3 |
| 4,416,762 | 11/1983 | Akiyama | 204/183.3 |
| 4,440,638 | 4/1984 | Judy | 210/198.2 |

Primary Examiner—Ernest G. Therkorn
Attorney, Agent, or Firm—Moonray Kojima

[57] ABSTRACT

In an apparatus for conducting solubilization chromatography wherein a solvent consisting of a buffer and ionized micells is allowed to flow through a capillary tube whose both ends are connected to the plus and minus sides, respectively, of a DC source, then a sample is introduced into the capillary tube, components of the sample are separated by combination of dissolution phenomenon of the sample in the ionized micells and capillary electro-phoresis, and qualitative and quantitative analysis of the components is carried out; a three way joint is provided having a first opening connected to the capillary tube, a second opening connected to tubing for feeding the solvent and sample, and a third opening serving as a discharge outlet for residue solution of solvent and sample not introduced into the capillary tube; and means are provided for controlling the time the sample contacts an inlet of the capillary tube within the three way joint, whereby the quantity of sample introduced into the capillary tube is controlled. In another embodiment, means are provided for controlling the quantity of sample which is drawn into the capillary tube.

8 Claims, 14 Drawing Figures

SOLUBILIZATION CHROMATOGRAPHY

BACKGROUND OF THE INVENTION

1. Field of Invention

This invention relates to solubilization chromatography, and more particularly, to improvements in the apparatus for performing solubilization chromatography.

In the solubilization chromatography process a solvent, consisting of a buffer solution and ionized micells, is allowed to flow through a capillary tube having two ends thereof connected, respectively, to the plus side and minus side of a direct current electric source, and then a sample is introduced into the capillary tube. Components of the sample are separated by the combined effect of the dissolution phenomenon of the sample in the ionized micells, and the capillary electrophoresis. The components of the sample are analyzed qualitatively and quantitatively.

2. Discussion of the Prior Art

FIG. 1 depicts a known solubilization chromatography apparatus comprising a capillary tube 1 constiituting a column (made of, for example, fused silica), containers 2,3 each having contained therein a mixed solution of buffer solution and micells with the ends of capillary tube 1 being separately inserted into the containers. The micells are, for example, colloid ions formed by dissolving sodium dodecyl sulfate (SDS) in the buffer solution. Electric source E has a plus side connected to an electrode 4 disposed in container 2 and a minus side connected to an electrode 5 disposed in container 3, and used to apply voltage to both ends of capillary tube 1. A detector 6, such as an ultraviolet spectrophotometer, is disposed on capillary tube 1 at a portion near electrode 5 of the minus side of source E.

As shown in FIG. 2, two phases of micells and buffer solution flow through capillary tube 1 having such configuration. Thus, when high voltage is applied to tube 1, the buffer solution flows in the direction of arrow A due to electro-osmosis flow. On the other hand, dissolved SDS (i.e. micells) is anions and, due to electrophoresis, has properties to transfer to a direction toward the plus side which direction is opposite to the direction of flow of the buffer solution. However, since the transfer velocity of the buffer solution is larger than that of micells by electro-phoresis, SDS micells, eventually, arrive at container 3 (minus side) after the buffer solution.

If a sample SM is injected into the plus side (i.e. where electrode 4 is located) tube 1, having the flow of the two phases within it, a component of the sample (which component is not soluble at all in the micells) is carried on an electro-osmosis stream, and it together with the buffer solution transfers to the minus side (i.e. where electrode 5 is located in container 3) at the fastest speed.

On the other hand, a component of the sample (which component is dissolved completely in the micells) transfers at the same speed as that of the micells and is delayed most in arriving at the minus side (i.e. where electrode 5 is located).

Moreover, an intermediate component of the sample (which component is soluble in the micells to some extent) transfers at a medium level of speed.

As a result, each component of the sample being transferred in capillary tube 1 has a retention time corresponding to a difference in solubilization ratio. Thus, if the thus separated components of the sample are detected by a detector 6, disposed on the outlet side of capillary tube 1, a chomatogram corresponding to the solubilization ratio of each sample component is obtained.

However, to carry out accurate analysis with such conventional apparatus, a constant quantity of sample is introduced into tube 1. This is done by controlling the quantity of sample introduced into tube 1 by setting a difference in height between containers 2 and 3 and using the head (i.e. pressure) difference thus created. However, with such a method, it is necessary to lift the sample container to obtain a desired head difference and also the work required is inefficient and unreliable in result. Furthermore, in the process of lifting the sample container, capillary tube 1 is often moved. Thus, it is difficult to reliably reproduce the measurements with such apparatus. In addition, disadvantageously, it is necessary to change the quantity of introduced sample, depending on the separation capacity of the capillary tube 1. Thus, it is difficult to control accurately the quantity of injected sample.

Accordingly, there are still many disadvantages and deficiencies in the prior art involving apparatus for practicing solubilization chromatography

SUMMARY OF THE INVENTION

Accordingly, an object of the invention is to overcome the aforementioned and other deficiencies and disadvantages of the prior art.

Another object is to provide an improved apparatus for performing solubilization chromatography, wherein mechanism is provided to easily control and change the quantity of sample introduced into the capillary tube.

The abovementioned and other objects are attained in the invention which encompasses an apparatus for performing solubilization chromatography, comprising a three way joint having a first opening connected to the capillary tube, a second opening connected to source of solvent and sample, and a third opening which serves to discharge any solution of solvent and sample which is not introduced into the capillary tube; and means for changing the contact time of the sample with the capillary tube within the three way joint. In another embodiment, means are provided, instead, for controlling the quantity of sample which is drawn into the capillary tube within the three way joint.

A feature of the invention is that the contact time of the sample with the inlet to the capillary tube is changed by changing the flow speed of the solvent, or by changing the quantity of sample injected into the three way joint through the second opening.

A further feature is that the quantity of sample drawn into the capillary tube is controlled by changing the magnitude of voltage applied to the two ends of the capillary tube, or by changing the duration of such voltage applied.

Another feature is that a supersonic piezoelectric transducer is mounted on the three way joint to introduce the sample into the capillary tube by supersonic vibrations and the quantity of sample drawn into the capillary tube is controlled by changing the magnitude or frequency of voltage applied to the transducer.

DETAILED DESCRIPTION OF THE PREFERRED EMBODIMENTS

Figure 1:
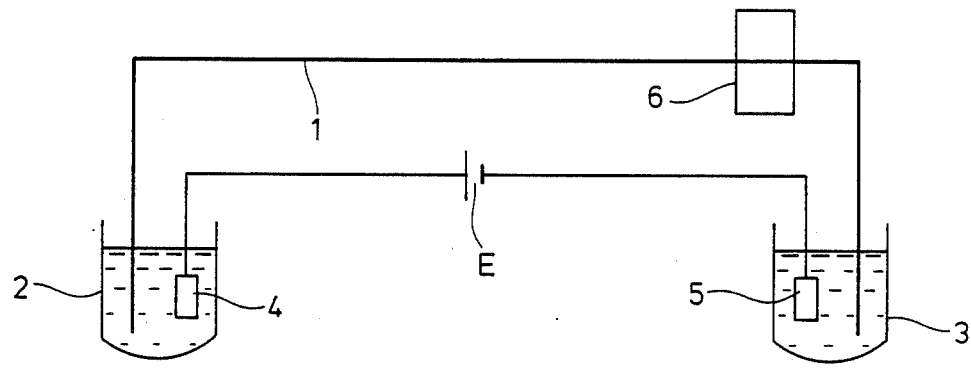
FIG. 1 is a pictorial view depicting a conventional apparatus for performing solubilization chromatography.
Figure 2:
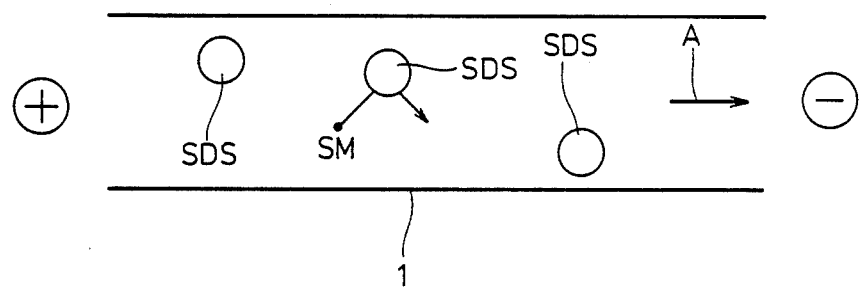
FIG. 2 is a diagram depicting component flow action of the embodiment of FIG. 1
Figure 3:
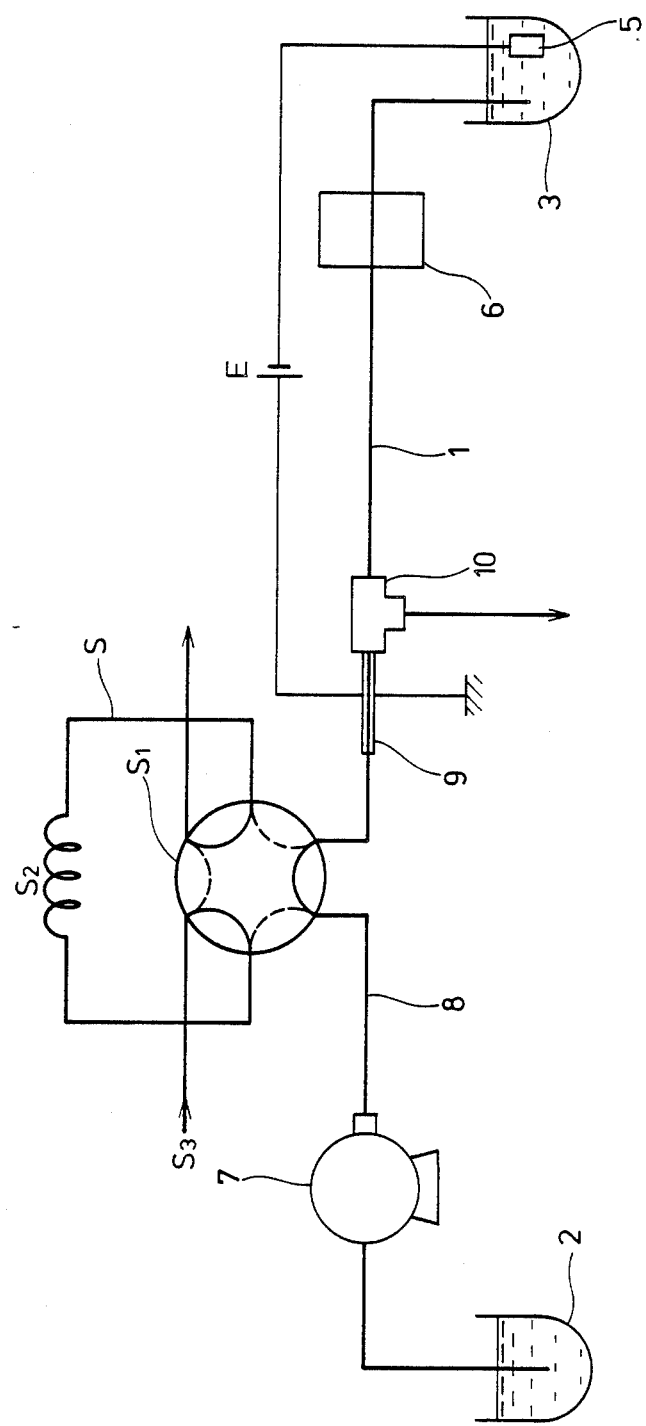
FIG. 3 is a pictorial view depicting an illustrative embodiment of the invention.
Figure 4:
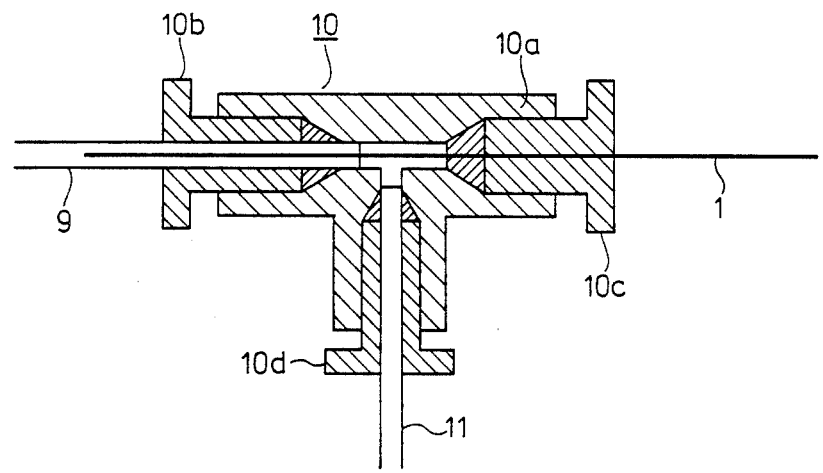
FIG. 4 is an enlarged sectional view of a part of the embodiment of FIG. 3.

Turning now to FIGS. 3, 4, elements which are substantially the same as those in FIG. 1 are marked with the same symbols and for clarity of description are not further discussed hereat. In FIGS. 3 and 4, low pressure pump 7 is used to send a solvent, consisting of a buffer solution and micells, from container 2 through tubing 8 to the downstream side, and constitutes a solvent feeding means.

A sample valve S is disposed in the middle of tubing 8 and comprises a six way switching valve $S_1$ and a measuring loop $S_2$. A given quantity of sample, fed through a sample injection port $S_3$, is injected into tubing 8 by change over of valve $S_1$. A tubular electrode 9 is connected to the end part of tubing 8 and is also connected to the plus side of electric source E.

A three way joint 10 has a first opening connected to capillary tube 1, a second opening connected to tubular electrode 9 through which the solvent and sample flow, and a third opening which is used as a discharge outlet. In FIG. 4, the three way joint is depicted comprising main body 10a, a clamping screw 10b for attaching tubular electrode 9 to main body 10a in the second opening, a clamping screw 10c for attaching capillary tube 1 to main body 10a in the first opening, and a clamping screw 10d for attaching a discharge tube 11 to main body 10a in the third opening.

Figure 5A:
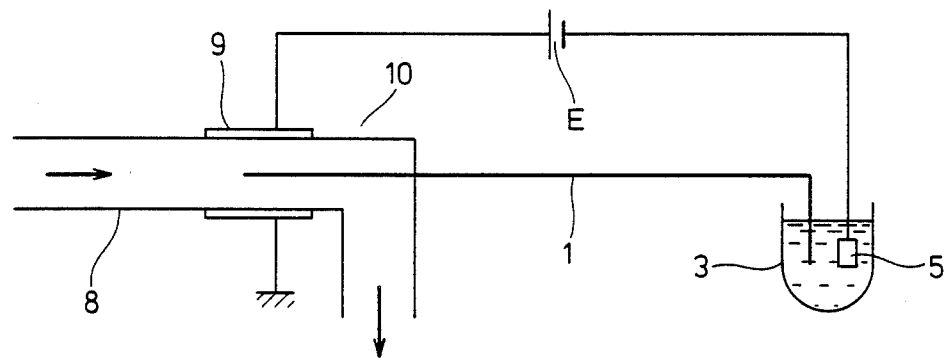
FIGS. 5(A), 5(B) and 5(C) are diagrams depicting flow action of the embodiment of FIG. 3.
Figure 5B:
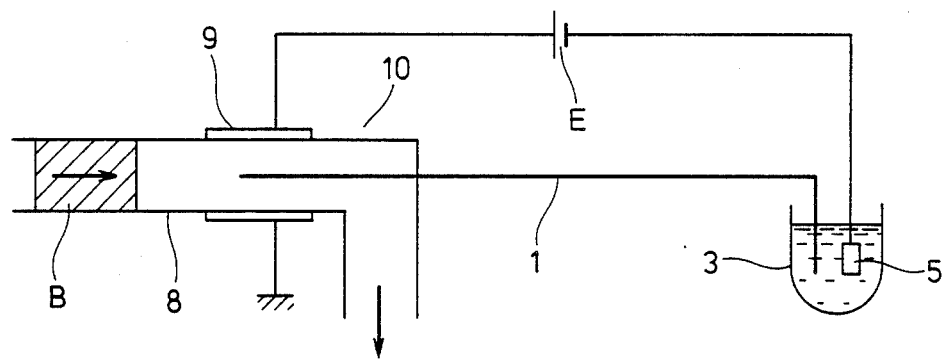
Figure 5C:
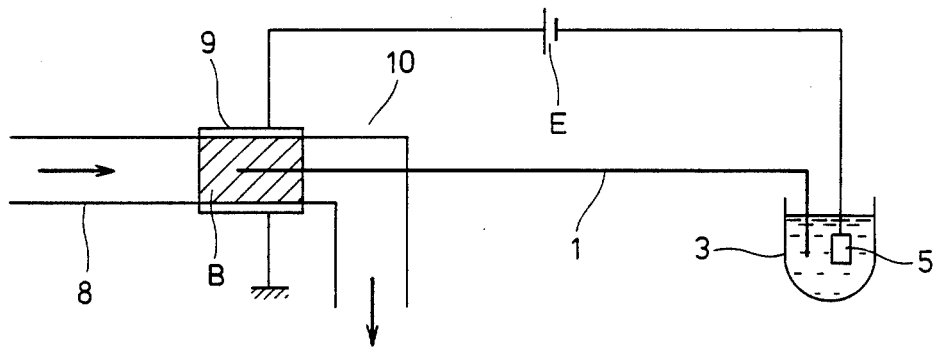

The flow action of the embodiment of FIGS. 3, 4 will now be described with reference to the diagrams of FIGS. 5(A), 5(B), and 5(C). FIG. 5(A) shows the state of the embodiment before the sample is injected into tubing 8. In this state, only the solvent, consisting of the buffer and micells, flows through the tubing 8, and the solvent is partially introduced into the capillary tube 1 by the electro-osmosis stream and by the electro-phoresis due to voltage supplied by source E. The residual solvent, having not been introduced into the capillary tube 1, is discharged through discharge outlet of the three way joint.

When sample B is injected into tubing 8 through sample valve S (see. FIG. 3), the sample B is sandwiched between two solvent parts, forming a band B, as shown in FIG. 5(B). Then, it is transferred with the solvent as fed by pump 7. When band B is brought into contact with the inlet tip of capillary tube 1 (see FIG. 5(C)), the sample is partially introduced into the tube 1 by the electroosmosis stream and by the electrophoresis, and the residual sample, having not been introduced into tube 1, is discharged through the discharge outlet of the three way joint, as in the case of the solvent.

In this process, the quantity of sample, introduced into capillary tube 1, is proportional to the contact time during which the sample B is in contact with the tip of the inlet of capillary tube 1, provided the applied voltage E is constant. Therefore, by controlling the contact time, it is possible to control the quantity of sample introduced into capillary tube 1.

For this purpose, in the embodiment of FIG. 3, as a first method, the speed of pump 7 is changed to change the contact time of band B with the inlet of capillary tube 1. As a second method, the measuring loop $S_2$ of sample valve S is changed and the quantity of sample introduced into tubing 8 through sample valve S is changed to change the width of the sample band B and thus change the contact time of band B with tip inlet of capillary tube 1.

By the above methods, the quantity of sample introduced into the capillary tube can be simply and efficiently controlled and changed. Also, capillary tube 1 need not be moved, such as is necessary in the prior art, to control and change the sample quantity. The quantity of sample introduced, so that reproducibility of the apparatus, is not diminished. Furthermore, analysis can be carried out without lowering capillary tube efficiency because the optimum quantity of sample introduced can be selected in conformity with the separation capacity of the capillary tube.

Figure 6:
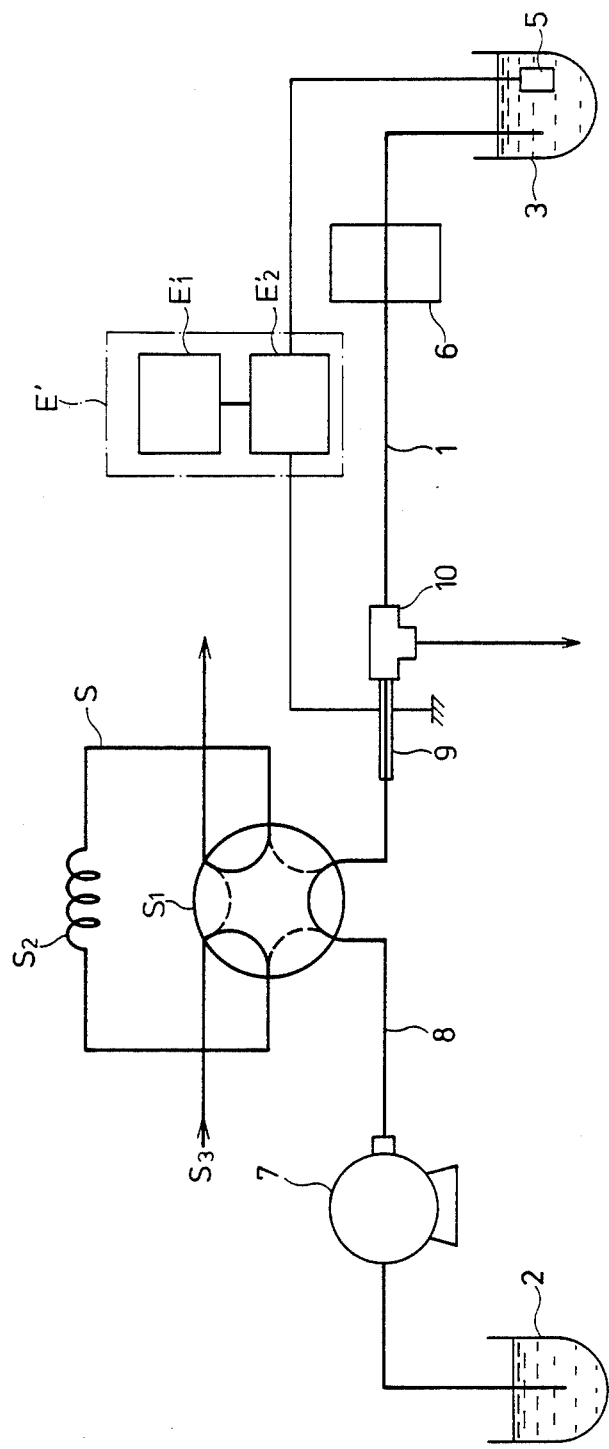
FIG. 6 is a pictorial view depicting another illustrative embodiment of the invention.

FIG. 6 depicts another illustrative embodiment wherein elements which are substantially the same as those in FIG. 3 are marked with the same symbols, and for clarity of description are not hereat discussed. The embodiment comprises a power supply E' (shown enclosed with an alternate long and short dash line), comprising an electric source $E_1'$ and a controller $E_2'$. Voltage from source $E_1'$ is applied through controller $E_2'$ to both ends of capillary tube 1.

If a quantity of sample injected through the sample valve S into tubing 8 is constant and the flow speed of solvent fed by pump 7 is constant, then the quantity of sample introduced into capillary tube 1 depends upon the magnitude of voltage applied to both ends of capillary tube 1, or upon the duration of the voltage applied.

In the embodiment of FIG. 6, in a state wherein a quantity of sample injected through sample valve S is set to be constant and the flow rate of solvent fed by pump 7 is set to be constant, the magnitude or duration of the applied voltage is controlled by controller $E_2'$ to control the quantity of sample introduced into capillary tube 1. By such a method, also, an effect similar to that in the embodiment of FIG. 3 can be obtained.

Figure 7:
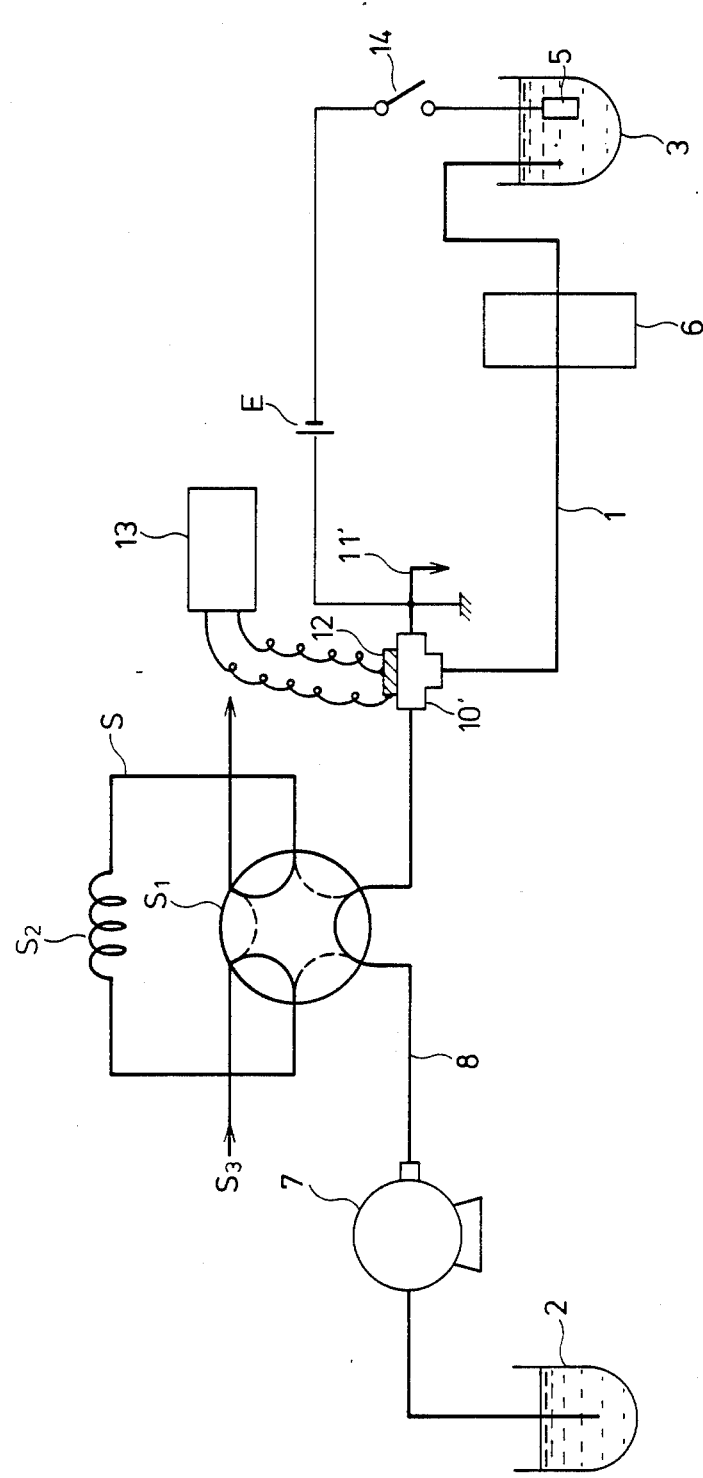
FIG. 7 is a pictorial view depicting a further illustrative embodiment of the invention.

FIG. 7 depicts a further illustrative embodiment, wherein elements substantially the same as those in FIGS. 3, 7 are marked with the same symbols and for clarity of description will not be hereat discussed further. In the embodiment, tubing 9 and tubular electrode 11', serving as a discharge tube, are connected to three way joint 10' and further a capillary tube 1 is connected to joint 10' with capillary tube 1 intersecting pipe line 8 at a right angle. A supersonic piezoelectric transducer 12 is mounted on joint 10' at a part thereof opposite to the tip inlet of capillary tube 1. An oscillator 13 drives supersonic piezoelectric transducer 12. A switch 14 controls connection of source E to both ends of tube 1.

Figure 8:
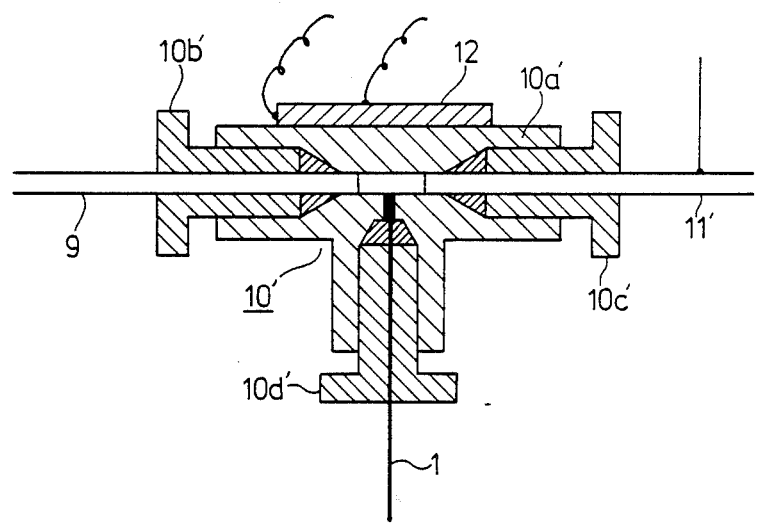
FIG. 8 is an enlarged sectional view of a part of the embodiment of FIG. 7.

FIG. 8 depicts an enlarged sectional view of the three way joint 10' of FIG. 7, wherein the joint 10' comprises a clamping screw 10b' for attaching tube 9 to main body 10' in the first opening, a clamping screw 10c' for attaching the tubular electrode 11', serving as a discharge tube, to main body 10' in the second opening, and a clamping screw 10d' for attaching capillary tube 1 to main body 10' in the third opening.

Figure 9:
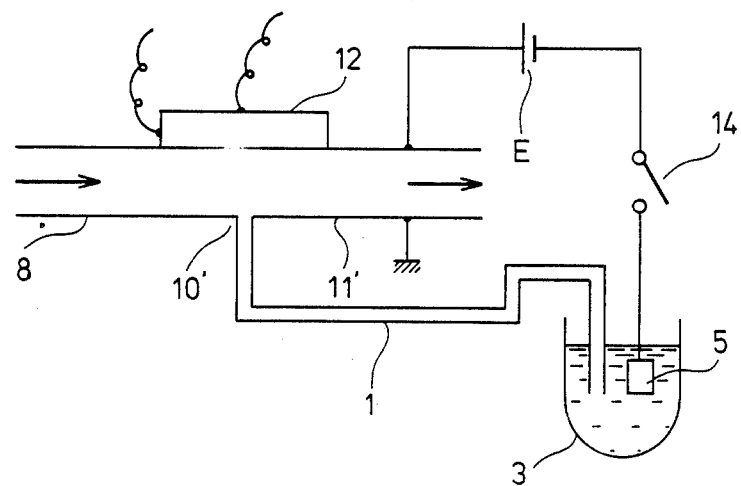
FIGS. 9(A), 9(B), 9(C), and 9(D) are diagrams depicting flow action of the embodiment of FIG. 7.
Figure 9:
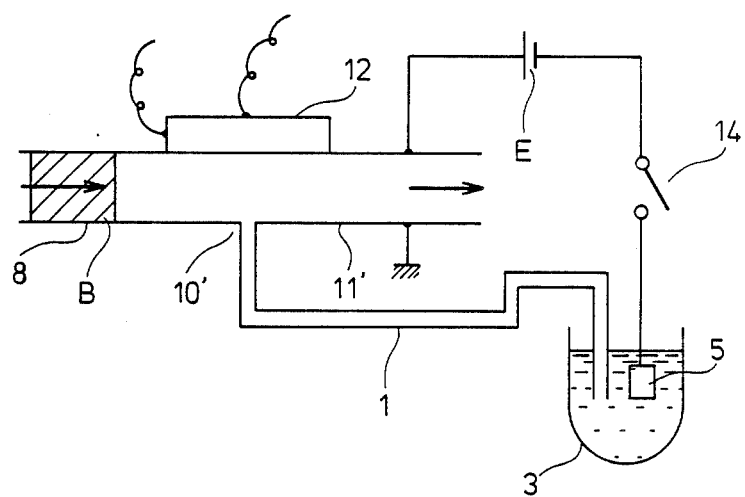
Figure 9:
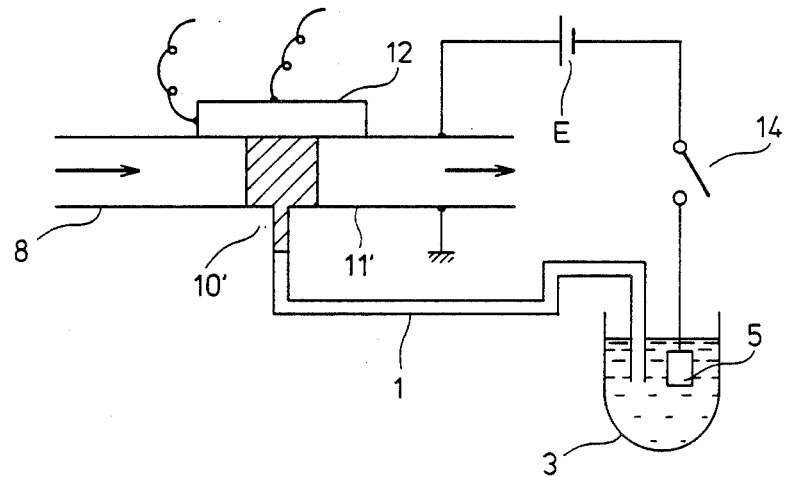
Figure 9:
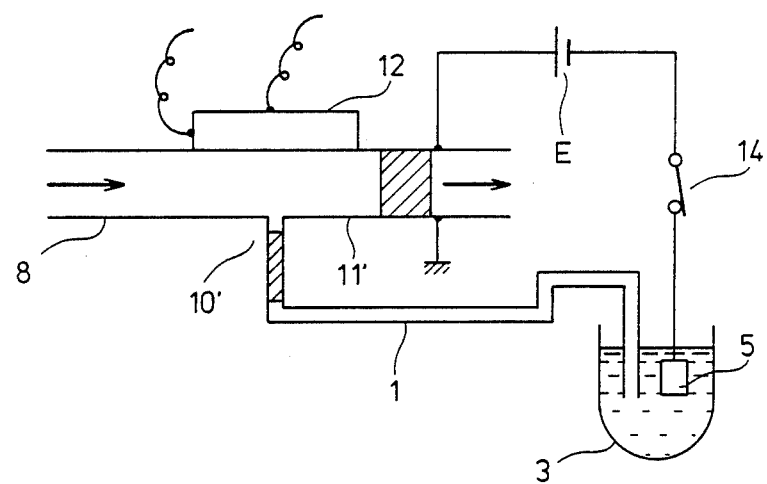

The flow action of the embodiment of FIG. 7 will now be described with reference to FIGS. 9(A), 9(B), 9(C), and 9(D), wherein FIG. 9(A) shows the state of the apparatus before the sample is injected into tube 8. In that state, switch 14 is OFF and solvent flows in the direction of the unmarked arrow in the three way joint 10'.

When the sample B is injected into tubing 8 through sample valve S, it is sandwiched between two parts of solvent, forming a band B, as shown in FIG. 9(B), and then it transfers with the flow of solvent. When band B arrives at the inlet tip of capillary tube 1, as shown in FIG. 9(C), supersonic piezoelectric transducer 12 is vibrated to inject the sample into capillary tube 1 forcibly by supersonic energy emitted toward the tip inlet. If the quantity of sample injected into tubing 8 through sample valve S is constant and the speed of the sample transferring in tube 8 is constant, then, the quantity of sample introduced into the capillary tube 1 is proportional to the magnitude or frequency of driving alternating voltage applied to supersonic piezoelectric transducer 12 from oscillator 13.

In the embodiment, in the state wherein the quantity of sample injected into the tubing through the sample valve S is set to be constant and the flow rate of solvent fed by the pump 7 is set to be constant, then, the quantity of sample introduced into capillary tube 1 is controlled by changing the magnitude or frequency of voltage applied to supersonic piezoelectric transducer 12.

After the band B passes over the inlet of the capillary tube 1 (see FIG. 9(D)) driving of supersonic piezoelectric transducer 12 is stopped and switch 14 is switched ON to apply voltage to both ends of capillary tube 1. The residual sample, having not been introduced into capillary tube 1, is discharged together with solvent through the discharge outlet, as depicted.

The sample thus introduced into capillary tube 1 is separated according to the principle of solubilization chromatography, and a chromatogram corresponding to the solubilization ratio of components of the sample, is obtained by detector 6 (see FIG. 7). In the embodiment, also, effects similar to that of the previous embodiments is obtained.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. An apparatus for performing solubilization chormatography, comprising
    capillary tube having two ends and with one of said ends serving as an inlet;
    direct current source having a positive side and a negative side, one end of said capillary tube being disposed on said positive side, and the other end being disposed on the negative side;
    means for supplying to said capillary tube a solvent comprising a buffer solution and ionized micells;
    means for introducing a sample into said capillary tube, whereby components of said sample are separated by the combined effect of dissolution phenomenon of said sample in said ionized micells and capillary electro-phoresis;
    tubing connected to said means for suppying and said means for introducing;
    three way joint comprising first, second and third openings, said first opening being connected to said inlet of said capillary tube, said second opening being connected to said tubing to supply said solvent and said sample, and said third opening serving as a discharge outlet for any residual solution of solvent and sample not introduced into said capillary tube, wherein within said three way joint a stream of said solution comprising said sample and said solvent is brought into contact with said inlet of said capillary tube;
    means for controlling the contact time of said sample with said inlet of said capillary tube thereby to control the quantity of said sample introduced into said capillary tube; and
    means for qualitative and quantitative analysis of said components of said sample.

2. The apparatus of claim 1, comprising means for changing the flow rate of said solvent, thereby to change the contact time of said sample with said inlet of said capillary tube.

3. The apparatus of claim 1, comprising means for changing quantity of sample injected into said tubing thereby to change the contact time of said sample with said inlet of said capillary tube.

4. An apparatus for performing solubilization chromatography, comprising
    capillary tube having two ends and with one of said ends serving as an inlet;
    direct current source having a positive side and a negative side, one end of said capillary tube being disposed on said positive side, and the other end being disposed on the negative side;
    means for supplying to said capillary tube a solvent comprising a buffer solution and ionized micells;
    means for introducing a sample into said capillary tube, whereby components of said sample are separated by the combined effect of dissolution phenomenon of said sample in said ionized micells and capillary electro-phoresis;
    tubing connected to said means for supplying and said means for introducing;
    three way joint comprising first, second and third openings, said first opening being connected to said inlet of said capillary tube, said second opening being connected to said tubing to supply said solvent and said sample, and said third opening serving as a discharge outlet for any residual solution of said sample and said solvent which is not introduced into said capillary tube, wherein within said three way joint a stream of said solution comprising said sample and said solvent is brought into contact with said inlet of said capillary tube;
    means for controlling the quantity of sample drawn into said inlet of said capillary tube; and
    means for qualitative and quantitative analysis of said components of said sample.

5. The apparatus of claim 4, comprising means for changing the magnitude of voltage applied to both ends of said capillary tube, thereby to control the quantity of sample drawn into said capillary tube.

6. The apparatus of claim 4, comprising means for changing the duration of voltage applied to both end of said capillary tube, thereby to control the quantity of sample drawn into said capillary tube.

7. The apparatus of claim 4, comprising a supersonic piezoelectric transducer mounted on said three way joint, and means for changing the magnitude of driving voltage applied to said transducer, thereby to control the quantity of sample drawn into said capillary tube.

8. The apparatus of claim 4, comprising a supersonic piezoelectric transducer mounted on said three way joint, and means for changing the frequency of alternating voltage used to drive said transducer, thereby to control the quantity of sample drawn into said capillary tube.

* * * * *